(12) United States Patent
Cawthorne et al.

(10) Patent No.: US 7,662,784 B2
(45) Date of Patent: Feb. 16, 2010

(54) METHOD FOR DECREASING BODY WEIGHT USING A SOMATOSTATIN RECEPTOR AGONIST

(75) Inventors: Michael Anthony Cawthorne, Bucks (GB); Yong-Ling Liu, Bucks (GB); Matthew V. Sennitt, Climping (GB)

(73) Assignee: Ipsen Pharma, S.A.S., Paris (FR)

( * ) Notice: Subject to any disclaimer, the term of this patent is extended or adjusted under 35 U.S.C. 154(b) by 0 days.

(21) Appl. No.: 11/289,800

(22) Filed: Nov. 29, 2005

(65) Prior Publication Data

US 2006/0205647 A1    Sep. 14, 2006

Related U.S. Application Data

(63) Continuation of application No. 09/423,684, filed as application No. PCT/EP98/02999 on May 13, 1998, now Pat. No. 7,034,003, which is a continuation of application No. 08/854,941, filed on May 13, 1997, now abandoned.

(51) Int. Cl.
*A61K 38/08*    (2006.01)
(52) U.S. Cl. .................................... 514/16
(58) Field of Classification Search ............... None
See application file for complete search history.

(56) References Cited

U.S. PATENT DOCUMENTS

| | | |
|---|---|---|
| 4,133,782 A | 1/1979 | Vale et al. |
| 4,146,612 A | 3/1979 | Veber |
| 4,190,575 A | 2/1980 | Sarantakis |
| 4,190,648 A | 2/1980 | Veber |
| 4,209,426 A | 6/1980 | Sarantakis |
| 4,211,693 A | 7/1980 | Rivier et al. |
| 4,215,039 A | 7/1980 | Sarantakis |
| 4,224,199 A | 9/1980 | Meyers et al. |
| 4,235,886 A | 11/1980 | Freidinger et al. |
| 4,238,481 A | 12/1980 | Rink et al. |
| 4,261,885 A | 4/1981 | Sakakibara et al. |
| 4,282,143 A | 8/1981 | Sarantakis |
| 4,291,022 A | 9/1981 | Sandrin et al. |
| 4,310,518 A | 1/1982 | Freidinger et al. |
| 4,316,890 A | 2/1982 | Kamber et al. |
| 4,328,214 A | 5/1982 | Rink et al. |
| 4,358,439 A | 11/1982 | Sieber et al. |
| 4,360,516 A | 11/1982 | Freidinger et al. |
| 4,369,179 A | 1/1983 | Rink et al. |
| 4,395,403 A | 7/1983 | Bauer et al. |
| 4,435,385 A | 3/1984 | Bauer et al. |
| 4,485,101 A | 11/1984 | Coy et al. |
| 4,486,415 A | 12/1984 | Freidinger |
| 4,522,813 A | 6/1985 | Nutt |
| 4,585,755 A | 4/1986 | Morgan et al. |
| 4,603,120 A | 7/1986 | Kamber |
| 4,650,787 A | 3/1987 | Schally et al. |
| 4,684,620 A | 8/1987 | Hruby et al. |
| 4,725,577 A | 2/1988 | Schally et al. |
| 4,728,638 A | 3/1988 | Bauer et al. |
| 4,853,371 A | 8/1989 | Coy et al. |
| 4,871,717 A | 10/1989 | Coy et al. |
| 4,904,642 A | 2/1990 | Coy et al. |
| 5,506,339 A | 4/1996 | Coy et al. |
| 5,583,104 A | 12/1996 | LaRusso |
| 5,708,135 A | 1/1998 | Coy et al. |
| 5,763,200 A | 6/1998 | Dunmore et al. |

FOREIGN PATENT DOCUMENTS

| | | |
|---|---|---|
| EP | 0 083 305 | 7/1983 |
| EP | 0 030 920 | 2/1984 |
| EP | 0 203 031 | 11/1986 |
| EP | 0 329 295 | 8/1989 |
| EP | 0 363 589 | 4/1990 |
| EP | 0 389 180 | 9/1990 |
| EP | 0 505 680 | 9/1992 |
| EP | 0 395 417 | 2/1995 |
| EP | 0657174 | 6/1995 |
| FR | 2 522 655 | 9/1983 |
| GB | 2 095 261 | 9/1982 |
| WO | 88/02756 | 4/1988 |
| WO | 88/05052 | 7/1988 |
| WO | 90/12811 | 11/1990 |
| WO | 91/09056 | 6/1991 |
| WO | WO 91/18016 | 11/1991 |
| WO | WO9635950 | 11/1996 |
| WO | WO 97/01579 | 1/1997 |
| WO | WO9711962 | 4/1997 |
| WO | WO9809991 | 3/1998 |
| WO | WO9810786 | 3/1998 |

OTHER PUBLICATIONS

Martinez et al. (1996) European Journal of Pharmacology, vol. 296, p. 153-160.*
Porzano et al. (1993) Diabetes Res., vol. 22, p. 3-10.*
J. Rudinger. In: Peptide Hormones, JA Parsons, Ed. (1976) 1-7.*
Lloyd et al.: American Physiological Society, vol. 268, pp. G102-G106, 1995.
Carretta, R. et al., "Reduction of Blood Pressure in Obese Hyperinsulinaemic Hypertensive Patients During Somatostatin Infusion", Journal of Hypertension, 7(6):S196-S197 (1989).

(Continued)

*Primary Examiner*—Andrew D Kosar
(74) *Attorney, Agent, or Firm*—Fish & Richardson; Alan F. Feeney; Pamela C. Ball

(57) ABSTRACT

The present invention relates to a method of decreasing body weight in a patient. The method includes the step of administering a therapeutically effective amount of a somatostatin or a somatostatin agonist to said patient. A pharmaceutical/cosmetic composition comprises the somatostatin or somatostatin agonist. Such products are used to prepare such compositions for the reduction or body weight in a human or mammalian animal.

10 Claims, No Drawings

OTHER PUBLICATIONS

Clark, J. A. et al., "Multiple Regions of Ligand Discrimination Revealed by Analysis of Chimeric Parathyroid Hormone 2 (PTH2) and PTH/PTH-Related Peptide (PTHrP) Receptors", Molecular Endocrinology, 12(2):193-206 (1998).

Horvath, A. et al., "Conformations of somatostatin analogues having antitumor activity," Peptides, 1992, Proceedings of the 22$^{nd}$ European Peptide Symposium, Sep. 13-19, 1992 Interlaken, Switzerland, p. 533-534.

Huang, H.-J. et al., " Hyperamylinemia, Hyperinsulinemia, and Insulin Resistance in Genetically Obese LA/N-*cp* Rats", Supplement to Hypertension, 19(1):I-101-1109 (1992).

Lunetta, M. et al., "Long-Term Octreotide Treatment Reduced Hyperinsulinemia, Excess Body Weight and Skin Lesions in Severe Obesity With Acanthosis Nigricans", J. Endocrinol. Invest., 19:699-703 (1996).

Van Binst, G. et al., "Backbone Modifications in Somatostatin Analogues: Relation Between Conformation and Activity", Peptide Research, 5(1):8-13 (1992).

Zamboni, M. et al., "Obesity and Regional Body-Fat Distribution in Men: Separate and Joint Relationships to Glucose Tolerance and Plasma Lipoproteins", *Am J Clin. Nutrition*, 60:682-687 (1994).

Shimon, I., et al., "Somatostatin receptor subtype specificity in human fetal pituitary cultures," 1997, J. Clin. Invest., 89:789-798.

* cited by examiner

METHOD FOR DECREASING BODY WEIGHT USING A SOMATOSTATIN RECEPTOR AGONIST

CROSS REFERENCE TO RELATED APPLICATIONS

This application is a continuation of U.S. application Ser. No. 09/423,684, filed Mar. 20, 2000, now U.S. Pat. No. 7,034,003, which is a National Phase Application under 35 U.S.C. 371 of PCT Application Serial Number PCT/EP98/02999, with an international filing date of May 13, 1998, which is a continuation of U.S. patent application Ser. No. 08/854,941, with a filing date of May 13, 1997, now abandoned.

INCORPORATION OF SEQUENCE LISTING

The application incorporates by reference in its entirety the Sequence Listing provided as a paper copy and on a diskette: 051 US PCT US-A Seq Listing.ST25.txt, created Dec. 7, 2007, 2 Kbytes in size.

This invention relates to a method and composition useful for reducing body weight in human or mammalian animal bodies.

BACKGROUND OF THE INVENTION

An estimated 35 million Americans are at least 20% overweight (Biotechnology 13:1060-1063 (1995)), a level at which health risks are significantly elevated. Nearly twice this number of Americans believe themselves to be overweight. A comparable picture is reported elsewhere. For example, in the United Kingdom, approximately one third of the women and 43% of the men are overweight, with at least one in six women and one in eight men classifiable as medically obese (Purnell, S., Highfield, The Daily Telegraph, Sep. 30, 1995). There, therefore, are both aesthetic and health reasons for weight control.

In the medically obese population, the condition is more severe and often associated with a myriad of serious medical problems such as non-insulin dependent diabetes mellitus, hypertension, dyslipidemia, coronary heart disease and musculoskeletal disorders. Thus, obesity is not just a problem of passive increase in adipose mass. It has been suggested that the underlying metabolic alterations in obesity may be amenable to therapeutic intervention (Goldstein, D. J., et al., Am. J. Clin. Nutr., 60:647-657 (1994)).

SUMMARY OF THE INVENTION

The present invention relates to a method of decreasing body weight in a patient (e.g., a mammal such as a human). The method includes the step of administering a therapeutically effective amount of somatostatin or a somatostatin agonist to said patient. The somatostatin or somatostatin agonist may be administered parenterally, e.g., administered intravenously, subcutaneously, or by implantation of a sustained release formulation. In one embodiment, the patient is obese (e.g., as defined by either 20-25% over normal body weight (Statistical Bulletin, Metropolitan Life Insurance Co., Vol. 40, pg. 1 (1959) or as defined by body mass index (BMI) greater than 25% over normal and including risk factors or a BMI greater than 30% over normal (see, e.g., Bray, G A and Gray, D S, Diabetes/Metabolism Review 4:653-679 (1988); Flynn, et al., Proc. Nutritional Society 50:413 (1991)). In another embodiment, the patient is a non-insulin dependent diabetic (i.e., type-2 diabetic).

The invention also comprises a pharmaceutical or cosmetic composition comprising a somatostatin or a somatostatin agonist. It further comprises the use of such compositions in the preparation of a pharmaceutical or cosmetic composition for the reduction of excessive body weight in a human or mammalian animal.

The term "somatostatin agonist" will be defined below. A therapeutically effective amount depends upon the condition being treated, the route of administration chosen, and the specific activity of the compound used and ultimately will be decided by the attending physician or veterinarian (e.g., between 5 µg/day to 5 mg/day). In one embodiment, the somatostatin agonist is administered to the patient until the patient has lost the requisite amount of body weight (e.g., the patient is no longer medically obese). In another embodiment, the somatostatin agonist is administered for the lifetime of the patient (e.g., maintaining normal body weight or secondary endpoints). In another embodiment, the somatostatin agonist is administered for cosmetic purposes.

The somatostatin agonist may be injected parenterally, e.g., intravenously, into the bloodstream of the subject being treated. However, it will be readily appreciated by those skilled in the art that the route, such as intravenous, subcutaneous, intramuscular, intraperitoneal, enterally, transdermally, transmucously, sustained released polymer compositions (e.g., a lactic acid polymer or copolymer microparticle or implant), profusion, nasal, oral, etc., will vary with the condition being treated and the activity and bioavailability of the somatostatin agonist being used.

While it is possible for the somatostatin agonist to be administered as the pure or substantially pure compound, it may also be presented as a pharmaceutical formulation or preparation. The formulations to be used in the present invention, for both humans and animals, comprise any of the somatostatin agonists to be described below, together with one or more pharmaceutically acceptable carriers thereof, and optionally other therapeutic ingredients.

The carrier must be "acceptable" in the sense of being compatible with the active ingredient(s) of the formulation (e.g., capable of stabilizing peptides) and not deleterious to the subject to be treated. Desirably, the formulation should not include oxidizing agents or other substances with which peptides are known to be incompatible. For example, somatostatin agonists in the cyclized form (e.g., internal cysteine disulfide bond) are oxidized; thus, the presence of reducing agents as excipients could lead to an opening of the cysteine disulfide bridge. On the other hand, highly oxidative conditions can lead to the formation of cysteine sulfoxide and to the oxidation of tryptophan. Consequently, it is important to carefully select the excipient. pH is another key factor, and it may be necessary to buffer the product under slightly acidic conditions (pH 5 to 6).

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary, as in the case of tablets, forming the product into the desired shape and size. Formulations suitable for parenteral (e.g., intravenous) administration, on the other hand, conveniently comprise sterile aqueous solutions of the active ingredient(s) Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

Formulations suitable for sustained release parenteral administrations (e.g., biodegradable polymer formulations such as polyesters containing lactic or glycolic acid residues) are also well known in the art. See, e.g., U.S. Pat. Nos. 3,773,919 and 4,767,628 and PCT Publication No. WO 94/15587.

The somatostatin or somatostatin agonist may also be administered with other antiobesity agents such as phentermine, diethylpropion, methamphetamine, phendimetrazine, phenmetrazine, diethylpropion, phentermine, mazindol, dextroamphetamine, phentermine, bezphetamine, orlistat, β3-adrenergic agonists (e.g., BTA-234 and SR58611A), sibutramine, henylpropanolamine, dexfenturamine, leptin, or bromocriptine.

Other features and advantages of the invention will be apparent from the following description of the preferred embodiments and from the claims.

ABBREVIATIONS

β-Nal=β-naphthylalanine
β-Pal=β-pyridylalanine
hArg(Bu)=N-guanidino-(butyl)-homoarginine
hArg(Et)$_2$=N,N'-guanidino-(dimethyl)-homoarginine
hArg(CH$_2$CF$_3$)$_2$=N,N'-guanidino-bis-(2,2,2-trifluoroethyl)-homoarginine
hArg(CH$_3$, hexyl)=N,N'-guanidino-(methyl, hexyl)-homoarginine
Lys(Me)=N-methyllysine
Lys(iPr)=N-isopropyllysine
AmPhe=aminomethylphenylalanine
AChxAla=aminocyclohexylalanine
Abu=α-aminobutyric acid
Tpo=4-thiaproline
MeLeu=N-methylleucine
Orn=ornithine
Nle=norleucine
Nva=norvaline
Trp(Br)=5-bromo-tryptophan
Trp(F)=5-fluoro-tryptophan
Trp(NO$_2$)=5-nitro-tryptophan
Gaba=γ-aminobutyric acid
Bmp=β-mercaptopropionyl
Ac=acetyl
Pen=pencillamine

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

Somatostatin and its Agonists

Somatostatin (somatotropin release inhibiting factor or SRIF) has both a 14 amino acid isoform (somatostatin-14) and a 28 amino acid isoform (somatostatin-28). See Wilson, J. & Foster, D., *Williams Textbook of Endocrinology*, p. 510 (7th ed., 1985). The compound is an inhibitor of secretion of the growth hormone and was originally isolated from the hypothalamus. Brazeau, et al., Science 179:77 (1973). Native somatostatin has a very short duration of effect in vivo since it is rapidly inactivated by endo- and exopeptidase. Many novel analogs have been prepared in order to enhance the duration of effect, biological activity, and selectivity (e.g., for the particular somatostatin receptor) of this hormone. Such analogs will be called "somatostatin agonists" herein.

Various somatostatin receptors (SSTRs) have been isolated, e.g., SSTR-1, SSTR-2, SSTR-3, SSTR-4, and SSTR-5. Thus, the somatostatin agonist may be a SSTR-1 agonist, SSTR-2 agonist, SSTR-3 agonist, SSTR-4 agonist or an SSTR-5 agonist. In one embodiment, the somatostatin agonist of the present invention is an SSTR-5 agonist or an SSTR-2 agonist. What is meant by an "SSTR-5 agonist" or an "SSTR-2 agonist" is a compound which (1) has a high affinity (e.g., Ki of less than 1 µM or, preferably, of less than 10 nM, or less than 2 nM, or of less than 1 nM) for the SSTR-5 or SSTR-2, respectively (e.g., as defined by the receptor binding assay described below), and (2) decreases body weight of a patient (e.g., as defined by the biological assay described below). The somatostatin agonist may also be selective for a particular somatostatin receptor, e.g., have a higher binding affinity for a particular somatostatin receptor subtype as compared to the other receptor subtypes. In one embodiment, the somatostatin receptor is an SSTR-5 selective agonist or SSTR-2 selective agonist. What is meant by an SSTR-5 selective agonist is a somatostatin agonist which (1) has a higher binding affinity (i.e., Ki) for SSTR-5 than for either SSTR-1, SSTR-2, SSTR-3, or SSTR-4 and (2) decreases body weight of a patient (e.g., as defined by the biological assay described below). In one embodiment, the SSTR-5 selective agonist has a Ki for SSTR-5 that is at least 2 times (e.g., at least 5 times or at least 10 times) less than its Ki for the SSTR-2 receptor (e.g., as defined by the receptor binding assay described below).

Somatostatin agonists which can be used to practice the therapeutic method of the present invention include, but are not limited to, those covered by formulae or those specifically recited in the publications set forth below, all of which are hereby incorporated by reference.

EP Application No. P5 164 EU (Inventor: G. Keri);
Van Binst, G. et al. Peptide Research 5:8 (1992);
Horvath, A. et al. Abstract, "Conformations of Somatostatin Analogs Having Antitumor Activity", 22nd European peptide Symposium, Sep. 13-19, 1992, Interlaken, Switzerland;
PCT Application WO 91/09056 (1991);
EP Application 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987)
U.S. Pat. No. 4,650,787 (1987);
U.S. Pat. No. 4,603,120 (1986);
U.S. Pat. No. 4,585,755 (1986);
EP Application 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);

U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,190 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Patent No. 0 389 180 (1990);
EP Application No. 0 505 680 (1982);
EP Application No. 0 083 305 (1982);
EP Application No. 0 030 920 (1980);
PCT Application No. WO 88/05052 (1988);
PCT Application No. WO 90/12811 (1990);
PCT Application No. WO 97/01579 (1997);
PCT Application No. WO 91/18016 (1991);
U.K. Application No. GB 2,095,261 (1981); and
French Application No. FR 2,522,655 (1983).

Examples of somatostatin agonists include, but are not limited to, the following somatostatin analogs which are disclosed in the above-cited references:

H-D-β-Nal-Cys-Tyr-D-Trp-Lys-Thr-Cys-Thr-NH$_2$ (BIM-23014);
H-D-Phe-Cys-Phe-D-Trp-Lys-Thr-Cys-β-Nal-NH$_2$;
H-D-Phe-Cys-Tyr-D-Trp-Lys-Thr-Cys-β-Nal-NH$_2$;
H-D-β-Nal-Cys-Phe-D-Trp-Lys-Thr-Cys-Thr-NH$_2$;
H-D-Phe-Cys-Tyr-D-Trp-Lys-Thr-Pen-Thr-NH$_2$;
H-D-Phe-Cys-Phe-D-Trp-Lys-Thr-Pen-Thr-NH$_2$;
H-D-Phe-Cys-Tyr-D-Trp-Lys-Thr-Pen-Thr-OH;
H-D-Phe-Cys-Phe-D-Trp-Lys-Thr-Pen-Thr-OH;
H-Gly-Pen-Phe-D-Trp-Lys-Thr-Cys-Thr-OH;
H-Phe-Pen-Tyr-D-Trp-Lys-Thr-Cys-Thr-OH;
H-Phe-Pen-Phe-D-Trp-Lys-Thr-Pen-Thr-OH;
H-D-Phe-Cys-Phe-D-Trp-Lys-Thr-Cys-Thr-ol (Octreotide);
H-D-Phe-Cys-Phe-D-Trp-Lys-Thr-Cys-Thr-NH$_2$;
H-D-Trp-Cys-Tyr-D-Trp-Lys-Val-Cys-Thr-NH$_2$;
H-D-Trp-Cys-Phe-D-Trp-Lys-Thr-Cys-Thr-NH$_2$;
H-D-Phe-Cys-Tyr-D-Trp-Lys-Val-Cys-Thr-NH$_2$;
H-D-Phe-Cys-Tyr-D-Trp-Lys-Val-Cys-Trp-NH$_2$;
H-D-Phe-Cys-Tyr-D-Trp-Lys-Val-Cys-Thr-NH$_2$;
Ac-D-Phe-Lys*-Tyr-D-Trp-Lys-Val-Asp-Thr-NH$_2$ (an amide bridge formed between Lys* and Asp);
Ac-hArg(Et)$_2$-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NH$_2$;
Ac-D-hArg(Bu)-Gly-Cys-Phe-D-Trp-Lys-Thr-Cys-Thr-NH$_2$;
Ac-D-hArg(Et)$_2$-Cys-Phe-D-Trp-Lys-Thr-Cys-Thr-NH$_2$;
Ac-L-hArg(Et)$_2$-Cys-Phe-D-Trp-Lys-Thr-Cys-Thr-NH$_2$;
Ac-D-hArg(CH$_2$CF$_3$)$_2$-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Phe-NH$_2$;
Ac-D-hArg(CH$_2$CF$_3$)$_2$-Gly-Cys-Phe-D-Trp-Lys-Thr-Cys-Thr-NHEt;
Ac-L-hArg(CH$_2$—CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys(Me)-Thr-Cys-Thr-NH$_2$;
Ac-D-hArg(CH$_2$CF$_3$)$_2$-Gly-Cys-Phe-D-Trp-Lys(Me)-Thr-Cys-Thr-NHEt;
Ac-hArg(CH$_3$, hexyl)-Gly-Cys-Phe-D-Trp-Lys-Thr-Cys-Thr-NH$_2$;
H-hArg(hexyl$_2$)-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NHEt;
Ac-D-hArg(Et)$_2$-Gly-Cys-Phe-D-Trp-Lys-Thr-Cys-Phe-NH$_2$;
Propionyl-D-hArg(Et)$_2$-Gly-Cys-Phe-D-Trp-Lys(iPr)-Thr-Cys-Thr-NH$_2$;
Ac-D-β-Nal-Gly-Cys-Phe-D-Trp-Lys-Thr-Cys-Gly-hArg(Et)$_2$-NH$_2$;
Ac-D-Lys(iPr)-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Phe-NH$_2$;
Ac-D-hArg(Et)$_2$-D-hArg(Et)$_2$-Gly-Cys-Phe-D-rp-Lys-Thr-Cys-Thr-NH$_2$;
Ac-Cys-Lys-Asn-4-Cl-Phe-Phe-D-Trp-Lys-Thr-Phe-Thr-Ser-D-Cys-NH$_2$;
H-Bmp-Tyr-D-Trp-Lys-Val-Cys-Thr-NH$_2$;
H-Bmp-Tyr-D-Trp-Lys-Val-Cys-Phe-NH$_2$;
H-Bmp-Tyr-D-Trp-Lys-Val-Cys-p-Cl-Phe-NH$_2$;
H-Bmp-Tyr-D-Trp-Lys-Val-Cys-β-Nal-NH$_2$;
H-D-β-Nal-Cys-Tyr-D-Trp-Lys-Val-Cys-Thr-NH$_2$;
H-D-Phe-Cys-Tyr-D-Trp-Lys-Abu-Cys-Thr-NH$_2$;
H-D-Phe-Cys-Tyr-D-Trp-Lys-Abu-Cys-β-Nal-NH$_2$;
H-pentafluoro-D-Phe-Cys-Tyr-D-Trp-Lys-Val-Cys-Thr-NH$_2$;
Ac-D-β-Nal-Cys-pentafluoro-Phe-D-Trp-Lys-Val-Cys-Thr-NH$_2$;
H-D-β-Nal-Cys-Tyr-D-Trp-Lys-Val-Cys-β-Nal-NH$_2$;
H-D-Phe-Cys-Tyr-D-Trp-Lys-Val-Cys-β-Nal-NH$_2$;
H-D-β-Nal-Cys-Tyr-D-Trp-Lys-Abu-Cys-Thr-NH$_2$;
H-D-p-Cl-Phe-Cys-Tyr-D-Trp-Lys-Abu-Cys-Thr-NH$_2$;
Ac-D-p-Cl-Phe-Cys-Tyr-D-Trp-Lys-Abu-Cys-Thr-NH$_2$;
H-D-Phe-Cys-β-Nal-D-Trp-Lys-Val-Cys-Thr-NH$_2$;
H-D-Phe-Cys-Tyr-D-Trp-Lys-Cys-Thr-NH$_2$;
cyclo(Pro-Phe-D-Trp-N-Me-Lys-Thr-Phe);
cyclo(Pro-Phe-D-Trp-N-Me-Lys-Thr-Phe);
cyclo(Pro-Phe-D-Trp-Lys-Thr-N-Me-Phe);
cyclo(N-Me-Ala-Tyr-D-Trp-Lys-Thr-Phe);
cyclo(Pro-Tyr-D-Trp-Lys-Thr-Phe);
cyclo(Pro-Phe-D-Trp-Lys-Thr-Phe);
cyclo(Pro-Phe-L-Trp-Lys-Thr-Phe); (SEQ ID NO:1)
cyclo(Pro-Phe-D-Trp(F)-Lys-Thr-Phe);
cyclo(Pro-Phe-Trp(F)-Lys-Thr-Phe); (SEQ ID NO:2)
cyclo(Pro-Phe-D-Trp-Lys-Ser-Phe);
cyclo(Pro-Phe-D-Trp-Lys-Thr-p-Cl-Phe);
cyclo(D-Ala-N-Me-D-Phe-D-Thr-D-Lys-Trp-D-Phe);
cyclo(D-Ala-N-Me-D-Phe-D-Val-Lys-D-Trp-D-Phe);
cyclo(D-Ala-N-Me-D-Phe-D-Thr-Lys-D-Trp-D-Phe);
cyclo(D-Abu-N-Me-D-Phe-D-Val-Lys-D-Trp-D-Tyr);
cyclo(Pro-Tyr-D-Trp-t-4-AchxAla-Thr-Phe);
cyclo(Pro-Phe-D-Trp-t-4-AchxAla-Thr-Phe);
cyclo(N-Me-Ala-Tyr-D-Trp-Lys-Val-Phe);
cyclo (N-Me-Ala-Tyr-D-Trp-t-4-AchxAla-Thr-Phe);
cyclo (Pro-Tyr-D-Trp-4-Amphe-Thr-Phe);

cyclo (Pro-Phe-D-Trp-4-Amphe-Thr-Phe);
cyclo(N-Me-Ala-Tyr-D-Trp-4-Amphe-Thr-Phe);
cyclo(Asn-Phe-Phe-D-Trp-Lys-Thr-Phe-Gaba);
cyclo(Asn-Phe-Phe-D-Trp-Lys-Thr-Phe-Gaba-Gaba);
cyclo(Asn-Phe-D-Trp-Lys-Thr-Phe);
cyclo(Asn-Phe-Phe-D-Trp-Lys-Thr-Phe-NH(CH$_2$)$_4$CO);
cyclo(Asn-Phe-Phe-D-Trp-Lys-Thr-Phe-β-Ala);
cyclo(Asn-Phe-Phe-D-Trp-Lys-Thr-Phe-D-Glu)-OH;
cyclo(Phe-Phe-D-Trp-Lys-Thr-Phe);
cyclo(Phe-Phe-D-Trp-Lys-Thr-Phe-Gly);
cyclo(Phe-Phe-D-Trp-Lys-Thr-Phe-Gaba);
cyclo(Asn-Phe-Phe-D-Trp-Lys-Thr-Phe-Gly);
cyclo(Asn-Phe-Phe-D-Trp(F)-Lys-Thr-Phe-Gaba);
cyclo(Asn-Phe-Phe-D-Trp(NO$_2$)-Lys-Thr-Phe-Gaba);
cyclo(Asn-Phe-Phe-Trp(Br)-Lys-Thr-Phe-Gaba); (SEQ ID NO:3)
cyclo(Asn-Phe-Phe-D-Trp-Lys-Thr-Phe(I)-Gaba);
cyclo(Asn-Phe-Phe-D-Trp-Lys-Thr-Tyr(But)-Gaba);
cyclo(Bmp-Lys-Asn-Phe-Phe-D-Trp-Lys-Thr-Phe-Thr-Pro-Cys)-OH;
cyclo(Bmp-Lys-Asn-Phe-Phe-D-Trp-Lys-Thr-Phe-Thr-Pro-Cys)-OH;
cyclo(Bmp-Lys-Asn-Phe-Phe-D-Trp-Lys-Thr-Phe-Thr-Tpo-Cys)-OH;
cyclo(Bmp-Lys-Asn-Phe-Phe-D-Trp-Lys-Thr-Phe-Thr-Me-Leu-Cys)-OH;
cyclo(Phe-Phe-D-Trp-Lys-Thr-Phe-Phe-Gaba);
cyclo(Phe-Phe-D-Trp-Lys-Thr-Phe-D-Phe-Gaba);
cyclo(Phe-Phe-D-Trp(5F)-Lys-Thr-Phe-Phe-Gaba);
cyclo(Asn-Phe-Phe-D-Trp-Lys(Ac)-Thr-Phe-NH—(CH$_2$)$_3$—CO);
cyclo(Lys-Phe-Phe-D-Trp-Lys-Thr-Phe-Gaba);
cyclo(Lys-Phe-Phe-D-Trp-Lys-Thr-Phe-Gaba);
cyclo(Orn-Phe-Phe-D-Trp-Lys-Thr-Phe-Gaba);
H-Cys-Phe-Phe-D-Trp-Lys-Thr-Phe-Cys-NH$_2$ (BIM-23268);
H-Cys-Phe-Phe-D-Trp-Lys-Ser-Phe-Cys-NH$_2$ (BIM-23284);
H-Cys-Phe-Tyr-D-Trp-Lys-Thr-Phe-Cys-NH$_2$ (BIM-23295); and
H-Cys-Phe-Tyr(I)-D-Trp-Lys-Thr-Phe-Cys-NH$_2$ (BIM-23313).

Note that for all somatostatin agonists described herein, each amino acid residue represents the structure of —NH—C(R)H—CO—, in which R is the side chain (e.g., CH$_3$ for Ala) except for Thr-ol which means —NH—CH(CH(CH$_3$)OH)—CH$_2$—OH and Pro which means prolinyl. Lines between amino acid residues represent peptide bonds which join the amino acids. Also, where the amino acid residue is optically active, it is the L-form configuration that is intended unless D-form is expressly designated. A disulfide bridge is formed between the two free thiols (e.g., Cys, Pen, or Bmp residues); however, it is not shown.

Use of linear somatostatin agonists of the following formula is also within the invention:

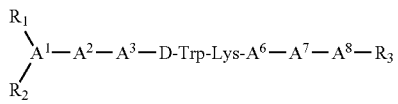

wherein $A^1$ is a D- or L-isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe, wherein X is CH$_3$, Cl, Br, F, OH, OCH$_3$ or NO$_2$;

$A^2$ is Ala, Leu, e, Val, Nle, Phe, β-Nal, pyridyl-Ala, Trp, 2,4-dichloro-Phe, pentafluoro-Phe, c-X-Phe, or p-X-Phe, wherein X is CH$_3$, Cl, Br, F, OH, OCH$_3$ or NO$_2$;

$A^3$ is pyridyl-Ala, Trp, Phe, β-Nal, 2,4-dichloro-Phe, pentafluoro-Phe, o-X-Phe, or p-X-Phe, wherein X is CH$_3$, Cl, Br, F, OH, OCH$_3$ or NO$_2$;

$A^6$ is Val, Ala, Leu, Ile, Nle, Thr, Abu, or Ser;

$A^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

$A^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe, wherein X is CH$_3$, Cl, Br, F, OH, OCH$_3$ or NO$_2$;

each $R_1$ and $R_2$, independently, is H, lower acyl or lower alkyl; and $R_3$ is OH or NH$_2$; provided that at least one of $A^1$ and $A^8$ and one of $A^2$ and $A^7$ must be an aromatic amino acid; and further provided that $A^1$, $A^2$, $A^7$ and $A^8$ cannot all be aromatic amino acids.

Examples of linear agonists to be used in the method of this invention include:

H-D-Phe-p-chloro-Phe-Tyr-D-Trp-Lys-Thr-Phe-Thr-NH$_2$;

H-D-Phe-p-NO$_2$-Phe-Tyr-D-Trp-Lys-Val-Phe-Thr-NH$_2$;

H-D-Nal-p-chloro-Phe-Tyr-D-Trp-Lys-Val-Phe-Thr-NH$_2$;

H-D-Phe-Phe-Phe-D-Trp-Lys-Thr-Phe-Thr-NH$_2$(BIM-23052);

H-D-Phe-Phe-Tyr-D-Trp-Lys-Val-Phe-Thr-NH$_2$;

H-D-Phe-p-chloro-Phe-Tyr-D-Trp-Lys-Val-Phe-Thr-NH$_2$; and

H-D-Phe-Ala-Tyr-D-Trp-Lys-Val-Ala-β-D-Nal-NH$_2$.

If desired, one or more chemical moieties, e.g., a sugar derivative, mono or poly-hydroxy C$_{2-12}$ alkyl, mono or poly-hydroxy C$_{2-12}$ acyl groups, or a piperazine derivative, can be attached to the somatostatin agonist, e.g., to the N-terminus amino acid. See PCT Application WO 88/02756, European Application 0 329 295, and PCT Application No. WO 94/04752. An example of a somatostatin agonists which contain N-terminal chemical substitutions are:

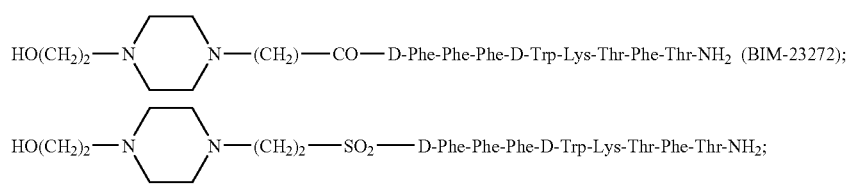

-continued

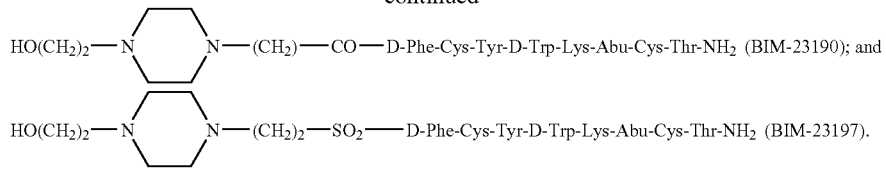

Synthesis of Somatostatin Agonists

The methods for synthesizing somatostatin agonists is well documented and are within the ability of a person of ordinary skill in the art.

Synthesis of short amino acid sequences is well established in the peptide art. For example, synthesis of H-D-Phe-Phe-Phe-D-Trp-Lys-Thr-Phe-Thr-NH$_2$, described above, can be achieved by following the protocol set forth in Example I of European Patent Application 0 395 417 A1. The synthesis of somatostatin agonists with a substituted N-terminus can be achieved, for example, by following the protocol set forth in WO 88/02756, European Patent Application No. 0 329 295, and PCT Publication No. WO 94/04752.

Somatostatin Receptor Binding Assays

The human SSTR-1, SSTR-2, SSTR-3, SSTR-4, and SSTR-5 cDNA clones have been described (SSTR-1 and SSTR-2 in Yamada, Y., et al., Proc. Natl. Acad. Sci. USA, 89:251-255 (1992); SSTR-3 in Yamada, et al., Mol. Endocrinol. 6:2136-2142 (1993); and SSTR-4 and SSTR-5 in Yamada, et al., Biochem. Biophys. Res. Commun. 195:844-852 (1993)) and are also available from American Type Culture Collection (ATCC, Rockville, Md.) (ATCC Nos. 79044 (SSTR-1), 79046 (SSTR-2), and 79048 (SSTR-3)). Based on the restriction endonuclease maps, the entire coding region of each SSTR cDNA may be excised by suitable restriction endonuclease digestion (Maniatis, T., et al., *Molecular Cloning—A Laboratory Manual*, CSHL, 1982). Restriction endonucleases are available from New England Biolabs (Beverly, Mass.). This cDNA fragment was inserted into the mammalian expression vector, pCMV (Russell, D., et al., J. Biol. Chem., 264:8222-8229 (1989)), using standard molecular biology techniques (see e.g., Maniatis, T., et al., Molecular Cloning,—A Laboratory Manual, Cold Spring Harbor Laboratory, 1982) to produce the expression plasmid, pCMV-human SSTR-1 through pCMV-human SSTR-5. Other mammalian expression vectors include pcDNA1/Amp (Invitrogen, Sandlesy, Calif.). The expression plasmids were introduced into the suitable bacterial host, *E. Coli* HB101 (Stratagene, La Jolla, Calif.) and plasmid DNAs, for transfection, were prepared on Cesium Chloride gradients.

CHO-K1 (ovary, Chinese hamster) cells were obtained from ATCC (ATCC No. CCL 61). The cells were grown and maintained in Ham's F12 media (Gibco BRL, Grand Island, N.Y.) supplemented with 10% fetal bovine serum under standard tissue culture conditions. For transfection, the cells were seeded at a density 1×10$^6$/60-cm plate (Baxter Scientific Products, McGaw Park, Ill.). DNA mediated transfection was carried out using the calcium phosphate co-precipitation method (Ausubel, F. M., et al., Current Protocols in Molecular Biology, John Wiley & Sons, 1987). The plasmid pRSV-neo (ATCC; ATCC No. 37198) was included as a selectable marker at 1/10 the concentration of the expression plasmid. CHO-K1 clonal cell lines that have stably inherited the transfected DNA were selected for growth in Ham's F12 media containing 10% fetal bovine serum and 0.5 mg/ml of G418 (Sigma). The cells were ring-cloned and expanded in the same media for analysis.

Expression of the human SSTR-1 through SSTR-5 receptors in the CHO-K1 cells were detected by Northern blot analysis of total RNA prepared from the cells (Sambrook, J. E., et al., Molecular Cloning—A Laboratory Manual, Ed. 2., Cold Spring Harbor Laboratory, Cold Spring Harbor, N.Y., 1989) and by receptor binding using [$^{125}$I-Tyr$^{11}$]somatostatin-14 as a ligand. Transfected cell lines expressing the human SSTR receptors were clonally expanded in culture and used in the following SSTR binding protocol.

Crude membranes were prepared by homogenization of the transfected cells in 20 ml of ice-cold 50 mM Tris-HCl with a POLYTRON homogenizer (setting 6, 15 sec). Buffer was added to obtain a final volume of 40 ml, and the homogenate was centrifuged in a Sorval SS-34 rotor at 39,000 g for 10 min at 0-4° C. The resulting supernatant was decanted and discarded. The pellet was rehomogenized in ice-cold buffer, diluted, and centrifuged as before. The final pellet was resuspended in the 10 mM Tris HCl and held on ice for the receptor binding assay.

Aliquots of the membrane preparation were incubated for 30 min at 30° C. with 0.05 nM [$^{125}$I-Tyr$^{11}$]somatostatin-14 (2000 Ci/mmol; Amersham Corp., Arlington Heights, Ill.) in 50 mM HEPES (pH 7.4) containing a test somatostatin agonist of various concentrations (e.g., $10^{-11}$ to $10^{-6}$), 10 mg/ml bovine serum albumin (fraction V) (Sigma Chemical Co., St. Louis, Mo.), MgCl$_2$ (5 mM), Trasylol (200 KIU ml), bacitracin (0.02 mg/ml), and phenylmethylsulphonyl fluoride (0.02 mg/ml). The final assay volume was 0.3 ml. The incubations were terminated by rapid filtration through GF/C filters (presoaked in 0.3% polyethylenimine for 30 min) using a Brandel filtration manifold. Each tube and filter were then washed three times with 5 ml aliquots of ice-cold buffer. Specific binding was defined as the total [$^{125}$I-Tyr$^{11}$]SRIF-14 bound minus that bound in the presence of 1000 nM. The Ki values for the tested somatostatin agonists were calculated by using the following formula: Ki=IC$_{50}$/[1+(LC/LEC)] where IC$_{50}$ is the concentration of test somatostatin agonist required to inhibit 50 percent of the specific binding of the radioligand [$^{125}$I-Tyr$^{11}$]somatostatin-14, LC is the concentration of the radioligand (0.05 nM), and LEC is the equilibrium dissociation constant of the radioligand (0.16 nM). The Ki values (nm) for the tested somatostatin agonists are shown in Table I.

TABLE I

| | hSSTR-1 | hSSTR-2 | hSSTR-3 | hSSTR-4 | hSSTR-5 |
|---|---|---|---|---|---|
| Somatostatin-14 | 2.26 | 0.23 | 1.2 | 1.8 | 1.41 |
| Somatostatin-28 | 2.38 | 0.30 | 1.3 | 7.93 | 0.4 |
| Octreotide | 875 | 0.57 | 26.8 | 5029 | 6.78 |

TABLE I-continued

| | hSSTR-1 | hSSTR-2 | hSSTR-3 | hSSTR-4 | hSSTR-5 |
|---|---|---|---|---|---|
| BIM-23014 | 2414 | 0.75 | 97.9 | 1826 | 5.21 |
| BIM-23052 | 97.6 | 11.96 | 5.6 | 127 | 1.22 |
| BIM-23190 | 9120 | 0.35 | 215 | 7537 | 11.1 |
| BIM-23197 | 6016 | 0.19 | 26.8 | 3897 | 9.81 |
| BIM-23272 | 47.7 | 3.23 | 10.9 | 753 | 1.01 |
| BIM-23284 | 27.9 | 19.3 | 35.6 | 58.6 | 0.85 |
| BIM-23295 | 86.9 | 6.19 | 9.7 | 3.4 | 0.34 |
| BIM-23313 | 15.1 | 4.78 | 25.5 | 55.3 | 0.30 |
| BIM-23268 | 1227 | 15.06 | 545 | 3551 | 0.42 |

Weight Loss Studies

The effect of chronic (6 day) treatment with BIM-23268 on body weight gain/loss was examined in an obese animal model, the fatty (fa/fa) Zucker rats (purchased from Harlan-Olac, Bicester, Oxon, U.K. See Bray, G., Federation Proceedings 36:148-153 (1977). Eleven male fatty Zucker rats weighing about 450 grams were randomly divided into two groups, and their initial body weights recorded. The animals were housed in pairs in a normal 12 hour light:12 hour darkness cycle at 20±2° C. and fed overnight ad libitum.

For the group assigned to receive drug treatment, the rats received the type-5 somatostatin receptor selective agonist BIM-23268C at 3 mg/kg, by subcutaneous injection twice a day at 10:00 a.m. and 5:00 p.m. The other group was treated with a subcutaneous injection of 0.1 ml/100 g of saline twice a day at 10:00 a.m. and 5:00 p.m. The animals were subjected to the BIM-23268 or saline treatment for a total of six days.

At 10:00 a.m. each day, food was removed and replaced with accurately weight 100 gram food pellet (a standard laboratory rat diet, Beekay rat and mouse diet, Bantin & Kingman, Hull, Humberside, U.K.). The amount of food remaining a 10:00 a.m. the next day was accurately weighed, recorded and replaced with 100 grams of fresh food pellets.

The animals were weighed each day during the 6-day treatment period at 5:00 p.m. The untreated control group mean weight was 414.09 at the start of the trial and was 418.89 after six days. The BIM-23268 treated group's mean weight was 413.6 at the start of the trial and remained at 413.6 after six days. The average food consumption for the control group was 26.0 g/rat/day and for the BIM-23268 group was 25.9 g/rat/day.

These results showed that body weight gain was lower in animals treated with BIM-23268. The effect on body weight change was not due to a toxic effect of the agent, as the treated group appeared healthy, and there was no difference in the amount of food consumed over the entire treatment period.

Secondary Endpoints of Efficacy

Because of the amount of weight that must be lost to achieve a clinically important alteration in risk for various sequelae of obesity, the Food and Drug Administration guidelines for the evaluation of weight-control drugs have recommended that additional endpoints showing a decrease in risk factors such as lipemia be monitored.

Obese (fa/fa) Zucker rats were treated as in example 1 above. On the last day of treatment (day 6), food was removed at 5:00 p.m., and the rats were fasted overnight. At 9:00 a.m. the next day, the animals were subjected to a glucose challenge, given as 0.8 gram/kg of glucose orally. Periodic 400 μl of blood samples were taken from the tail vein (Peterson, R. G., ILAR News, 32:16-19 (1990)) 60 min. and 30 min. before and at 30, 60, 90, and 120 min. after the administration of the glucose challenge (0.8 gram/kg orally). Aprotinin (Traysylol, Bayer UK, Hayward's Health, W. Sussex, U.K. and heparin (Sigma Chemical Co., Poole, Dorset, U.K.) were added to the blood samples to a final concentration of 400 KIU/ml and 100 units/ml, respectively. Plasma fractions were prepared from these samples by centrifugation at 4000×G in a microfuge, for the estimation of triglycerides and glycerol. Samples were then stored at −80° C. until assayed.

Plasma glycerol and triglycerides were determined using the Sigma Enzymatic (Tinder) calorimetric assay kit (Cat #337-B, Sigma Chemical Co., Poole, Dorset, U.K.) and measuring absorbance at 540 nm in a spectrophotometer.

After six days of treatment with BIM-23268C at 3 mg/kg twice a day by subcutaneous injection, both plasma glycerol and triglycerides were significantly lowered, as exemplified by the samples taken at time 30 and 60 minutes before the oral glucose challenge. The administration of an oral glucose challenge have no significant effect on plasma lipids. The BIM-23628C treated group showed a significantly lower plasma glycerol and triglycerides throughout the 2-hour test period. The results suggested that BIM-23268C, following a 6-day treatment period at the prescribed dose was effective in reducing hypertriglyceridemia.

Assessment of Efficacy in Patient

The effect of the somatostatin agonist on obesity can be examined in patients by assessing total body weight, body mass index, total adipose tissue content, subcutaneous tissue content, visceral adipose tissue content (see, e.g., Zamboni, M., Amer. J. Clin. Nutr. 60:682-687 (1994). The effect of the somatostatin agonist can also be measured on other secondary endpoints, such as insulin sensitivity (see, e.g., Bergman, R. N., et al., Endocrin. Rev. 6:45-86 (1985); Turner, R. C., Diabetes 44:1-10 (1995)), blood pressure (see, e.g., Maheux, P., Hypertension 24:695-698 (1994)), plasma lipids (see, e.g., Dubrey, S. W., et al., Diabetes 43:831-835 (1994)), and the other acceptable endpoints recommended by the FDA Draft Guidelines for the Clinical Evaluation of Weight Control Drugs (1994) (see also, Drug & Market Development 6:36 (1994)).

OTHER EMBODIMENTS

The foregoing description has been limited to specific embodiments of this invention. It will be apparent, however, that variations and modifications may be made to the invention, with the attainment of some or all of the advantages of the invention. Such embodiments are also within the scope of the following claims.

The invention claimed is:

1. A method of maintaining body weight or reducing body weight gain in an overweight patient, comprising the step of:

administering a therapeutically effective amount of a somatostatin type-5 receptor selective peptide agonist to an overweight patient;

wherein said effective amount of said somatostatin type-5 receptor selective peptide agonist results in a decrease of body weight and wherein said somatostatin type-5 receptor selective peptide agonist has a Ki for the somatostatin type-5 receptor that is at least 2 times less than the Ki for the somatostatin type-2 receptor.

2. A method according to claim 1 wherein the somatostatin agonist is

H-Cys-Phe-Phe-D-Trp-Lys-Thr-Phe-Cys-NH$_2$,

H-Cys-Phe-Phe-D-Trp-Lys-Ser-Phe-Cys-NH$_2$,

H-Cys-Phe-Tyr-D-Trp-Lys-Thr-Phe-Cys-NH$_2$ or

H-Cys-Phe-Tyr(I)-D-Trp-Lys-Thr-Phe-Cys-NH$_2$.

3. A method according to claim 1 wherein the somatostatin agonist is

H-D-Phe-Phe-Phe-D-Trp-Lys-Thr-Phe-Thr-NH$_2$.

4. A method according to claim 1 wherein the somatostatin agonist is

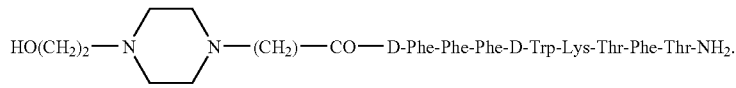

5. The method according to claim 1, wherein said decrease of body weight is measured by assessing total body weight.

6. The method according to claim 1, wherein said decrease of body weight is measured by assessing body mass index.

7. The method according to claim 1, wherein said decrease of body weight is measured by assessing total adipose tissue content.

8. The method according to claim 1, wherein said decrease of body weight is measured by assessing subcutaneous tissue content.

9. The method according to claim 1, wherein said decrease of body weight is measured by assessing visceral adipose tissue content.

10. The method according to claim 1, wherein said overweight patient is a non-insulin-dependent diabetic human.

* * * * *

SEQUENCE LISTING

<160> NUMBER OF SEQ ID NOS: 3

<210> SEQ ID NO 1

-continued

```
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: mis_feature
<223> OTHER INFORMATION: Cyclo-peptide

<400> SEQUENCE: 1

Pro Phe Trp Lys Thr Phe
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: mis_feature
<223> OTHER INFORMATION: Cyclo-peptide
<220> FEATURE:
<221> NAME/KEY: VARIANT
<222> LOCATION: 3
<223> OTHER INFORMATION: Trp(F)

<400> SEQUENCE: 2

Pro Phe Xaa Lys Trp Phe
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetically generated peptide
<220> FEATURE:
<221> NAME/KEY: mis_feature
<223> OTHER INFORMATION: Cyclo-peptide
<220> FEATURE:
<221> NAME/KEY: VARIANT
<222> LOCATION: 4
<223> OTHER INFORMATION: Trp(Br)
<220> FEATURE:
<221> NAME/KEY: VARIANT
<222> LOCATION: 8
<223> OTHER INFORMATION: Gaba

<400> SEQUENCE: 3

Asn Phe Phe Xaa Lys Thr Phe Xaa
1               5
```